(12) United States Patent
Takemoto

(10) Patent No.: US 12,632,914 B2
(45) Date of Patent: May 19, 2026

(54) MEDICAL IMAGE CAPTURING APPARATUS AND CONTROL METHOD OF THE SAME

(71) Applicant: FUJIFILM Healthcare Corporation, Chiba (JP)

(72) Inventor: Kazuma Takemoto, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 108 days.

(21) Appl. No.: 18/432,076

(22) Filed: Feb. 5, 2024

(65) Prior Publication Data

US 2024/0281917 A1 Aug. 22, 2024

(30) Foreign Application Priority Data

Feb. 16, 2023 (JP) ................................. 2023-022361

(51) Int. Cl.
| | |
|---|---|
| *G06T 1/00* | (2006.01) |
| *G16H 30/20* | (2018.01) |
| *G16H 30/40* | (2018.01) |

(52) U.S. Cl.
CPC .......... *G06T 1/0007* (2013.01); *G16H 30/20* (2018.01); *G16H 30/40* (2018.01); *G06T 2210/41* (2013.01)

(58) Field of Classification Search
CPC ... G06T 1/0007; G06T 2210/41; G16H 30/20; G16H 30/40

USPC ...................................................... 348/207.99
See application file for complete search history.

(56) References Cited

U.S. PATENT DOCUMENTS

2016/0058403 A1* 3/2016 Kim ...................... A61B 6/467
378/98.2
2020/0402272 A1 12/2020 Xu et al.

FOREIGN PATENT DOCUMENTS

| | | | |
|---|---|---|---|
| JP | 2021006993 | 1/2021 | |
| WO | WO-2022208414 A1 * | 10/2022 | ............. A61B 34/37 |

* cited by examiner

*Primary Examiner* — Joel W Fosselman
(74) *Attorney, Agent, or Firm* — JCIPRNET

(57) ABSTRACT

Provided are a medical image capturing apparatus and a control method of the same that eliminate a need for different adjustment of an imaging position for each facility or each operator.

There is provided a medical image capturing apparatus that captures a medical image of a subject, the medical image capturing apparatus including: a camera image acquisition unit that acquires a camera image of the subject; an imaging position setting unit that sets an imaging position based on the camera image; a storage unit that stores adjustment data related to the imaging position for each facility or for each operator; and an imaging position adjustment unit that adjusts the imaging position by using the adjustment data acquired from the storage unit based on an identifier for identifying the facility or the operator.

7 Claims, 7 Drawing Sheets

400
100
10
401
403
402
501
503
502
105

MEDICAL IMAGE CAPTURING APPARATUS AND CONTROL METHOD OF THE SAME

CLAIM OF PRIORITY

The present application claims priority from Japanese Patent Application JP 2023-022361 filed on Feb. 16, 2023, the content of which is hereby incorporated by reference into this application.

BACKGROUND OF THE INVENTION

1. Field of the Invention

The present invention relates to a medical image capturing apparatus that captures a medical image of a subject, and particularly, to a technique of adjusting an imaging position set with respect to the subject.

2. Description of the Related Art

A medical image capturing apparatus is an apparatus that detects a signal obtained from an imaging position of a subject, for example, X-rays transmitted through the subject, nuclear magnetic resonance signals generated from the subject, or the like, to capture a medical image to be used to diagnose the subject, or the like. In the medical image capturing apparatus, the imaging position is set with respect to the subject on an examination table prior to the capturing of the medical image. It is desirable that the setting of the imaging position be automated.

In JP2021-6993A, it is disclosed that 3D camera images are input into two trained independent deep learning models, and an imaging position is automatically set based on a prediction result obtained from each of the two.

SUMMARY OF THE INVENTION

However, JP2021-6993A lacks consideration for individually adjusting the automatically set imaging position for each facility or each operator. The imaging position is not necessarily limited to being set based on a uniform standard and may be individually adjusted based on facility policies or the operator's experience.

In that respect, an object of the present invention is to provide a medical image capturing apparatus and a control method of the same that eliminate a need for different adjustment of an imaging position for each facility or each operator.

In order to achieve the above-described object, according to an aspect of the present invention, there is provided a medical image capturing apparatus that captures a medical image of a subject, the medical image capturing apparatus comprising: a camera image acquisition unit that acquires a camera image of the subject; an imaging position setting unit that sets an imaging position based on the camera image; a storage unit that stores adjustment data related to the imaging position for each facility or for each operator; and an imaging position adjustment unit that adjusts the imaging position by using the adjustment data acquired from the storage unit based on an identifier for identifying the facility or the operator.

In addition, according to another aspect of the present invention, there is provided a control method of a medical image capturing apparatus that captures a medical image of a subject, the control method comprising: a camera image acquisition step of acquiring a camera image of the subject;

an imaging position setting step of setting an imaging position based on the camera image; and an imaging position adjustment step of adjusting the imaging position by using adjustment data related to the imaging position, the adjustment data being acquired based on an identifier for identifying a facility or an operator from a storage unit that stores the adjustment data for each facility or for each operator.

According to the present invention, it is possible to provide a medical image capturing apparatus and a control method of the same that eliminate a need for different adjustment of an imaging position for each facility or each operator.

DESCRIPTION OF THE PREFERRED EMBODIMENTS

Hereinafter, examples of a medical image capturing apparatus according to the present invention will be described with reference to the accompanying drawings. The medical image capturing apparatus is an apparatus that detects a signal obtained from a subject, for example, X-rays transmitted through the subject, nuclear magnetic resonance signals generated from the subject, or the like, to capture a medical image to be used to diagnose the subject, or the like. Hereinafter, as an example of the medical image capturing apparatus, an X-ray computed tomography (CT) apparatus that captures a tomographic image of the subject by acquiring X-ray projection images of the subject at various projection angles will be described.

Example 1

Figure 1:
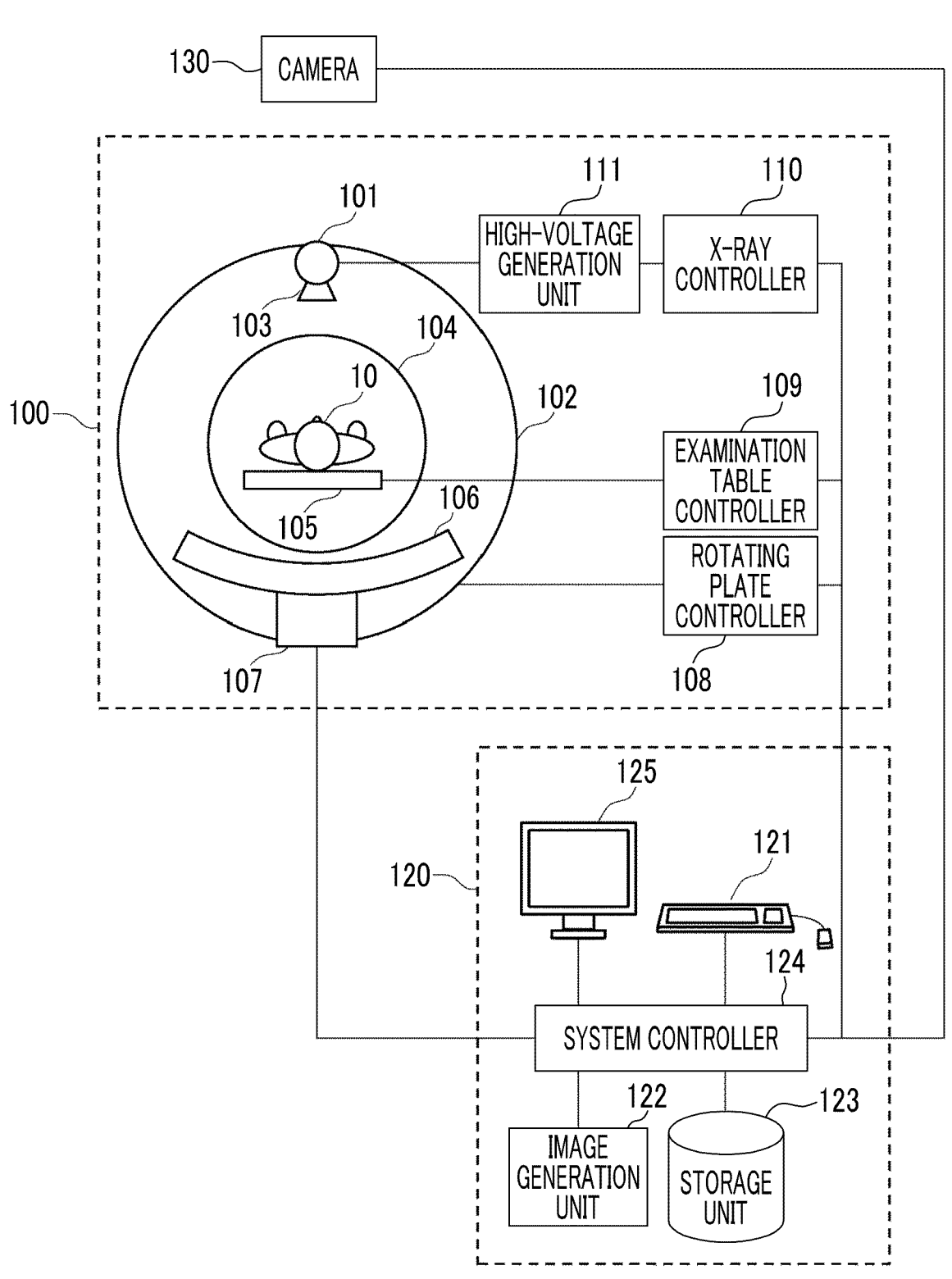
FIG. 1 is a diagram showing an example of an overall configuration of an X-ray CT apparatus of Example 1.

An overall configuration of the X-ray CT apparatus of Example 1 will be described with reference to FIG. 1. The X-ray CT apparatus comprises a scan gantry unit 100, an operation unit 120, and a camera 130. The scan gantry unit 100 and the camera 130 are installed in an imaging room surrounded by a shielding material that blocks X-rays, and the operation unit 120 is installed in an operation room located outside the imaging room.

The scan gantry unit 100 comprises an X-ray source 101, a rotating plate 102, a collimator 103, an X-ray detector 106, a data collection unit 107, an examination table 105, a rotating plate controller 108, an examination table controller 109, an X-ray controller 110, and a high-voltage generation unit 111. The X-ray source 101 is a device that irradiates a subject 10 placed on the examination table 105 with X-rays and is, for example, an X-ray tube device. The collimator 103 is a device that restricts an irradiation range of X-rays.

The rotating plate 102 is provided with an opening portion 104 through which the subject 10 placed on the examination table 105 enters, and is also equipped with the X-ray source 101 and the X-ray detector 106 and rotates the X-ray source 101 and the X-ray detector 106 around the subject 10.

The X-ray detector 106 is a device that is disposed to face the X-ray source 101, that comprises a plurality of detection elements which detect X-rays transmitted through the subject 10, and that detects a spatial distribution of X-rays, and functions as a detection unit that detects a signal obtained from the subject 10. The detection elements of the X-ray detector 106 are arranged two-dimensionally in a rotation direction and a rotation axis direction of the rotating plate 102. The data collection unit 107 is a device that collects the spatial distribution of X-rays detected by the X-ray detector 106 as digital data.

The rotating plate controller 108 is a device that controls rotation and inclination of the rotating plate 102. The examination table controller 109 is a device that controls up, down, front, back, left, and right movements of the examination table 105. The high-voltage generation unit 111 is a device that generates a high voltage applied to the X-ray source 101. The X-ray controller 110 is a device that controls an output of the high-voltage generation unit 111. The rotating plate controller 108, the examination table controller 109, and the X-ray controller 110 are, for example, a micro-processing unit (MPU) or the like.

The operation unit 120 comprises an input unit 121, an image generation unit 122, a display unit 125, a storage unit 123, and a system controller 124. The input unit 121 is a device that is used to input examination data such as a name of the subject 10, an examination date and time, and an imaging condition, and is, for example, a keyboard, a pointing device, a touch panel, or the like. The image generation unit 122 is a device that generates the tomographic image by using the digital data collected by the data collection unit 107, and is, for example, an MPU, a graphics processing unit (GPU), or the like. The display unit 125 is a device that displays the tomographic image or the like generated by the image generation unit 122, and is, for example, a liquid crystal display, a touch panel, or the like. The storage unit 123 is a device that stores the digital data collected by the data collection unit 107, the tomographic image generated by the image generation unit 122, a program to be executed by the system controller 124, data to be used by the program, and the like, and is, for example, a hard disk drive (HDD), a solid state drive (SSD), or the like. The system controller 124 is a device that controls each unit such as the rotating plate controller 108, the examination table controller 109, and the X-ray controller 110, and is, for example, a central processing unit (CPU).

The camera 130 is a device that images the subject 10 placed on the examination table 105 together with the examination table 105 from above, and is provided on a ceiling of the imaging room or above the scan gantry unit 100. A camera image captured by the camera 130 is displayed on the display unit 125, and is used by an operator in the operation room to confirm a state of the subject 10 or is used to set the imaging position. The camera image may be stored in the storage unit 123.

The high-voltage generation unit 111 generates a tube voltage, which is a high voltage applied to the X-ray source 101, based on the imaging condition set via the input unit 121, whereby X-rays corresponding to the imaging condition are emitted to the subject 10 from the X-ray source 101. The X-ray detector 106 detects the X-rays emitted from the X-ray source 101 and transmitted through the subject 10 with a large number of detection elements and acquires the spatial distribution of the transmitted X-rays. The rotating plate 102 is controlled by the rotating plate controller 108 and rotates based on the imaging condition input through the input unit 121, particularly a rotation speed or the like. The examination table 105 is controlled by the examination table controller 109 and moves relative to the rotating plate 102 to move the imaging position set with respect to the subject 10 to an imaging field of view, which is a range in which the transmitted X-rays are detected.

By repeating the irradiation of X-rays by the X-ray source 101 and the detection of X-rays by the X-ray detector 106 with the rotation of the rotating plate 102, projection data, which is the X-ray projection image of the subject 10, is measured at various projection angles. The projection data is associated with a view representing each projection angle, and a channel (ch) number and a column number which are detection element numbers of the X-ray detector 106. The measured projection data is transmitted to the image generation unit 122. The image generation unit 122 generates the tomographic image by performing back-projection processing on a plurality of pieces of projection data. The generated tomographic image is displayed on the display unit 125 or stored in the storage unit 123 as the medical image.

The imaging position that is automatically set by using the camera image obtained by imaging the subject 10 on the examination table 105 prior to the capturing of the tomographic image is based on a uniform standard and may be individually adjusted according to facility policies or the operator's experience. In that respect, in Example 1, the imaging position automatically set based on a uniform standard by using adjustment data prepared in advance for each facility or for each operator is adjusted, thereby eliminating the need for adjustment of the imaging position by the operator.

Figure 2:
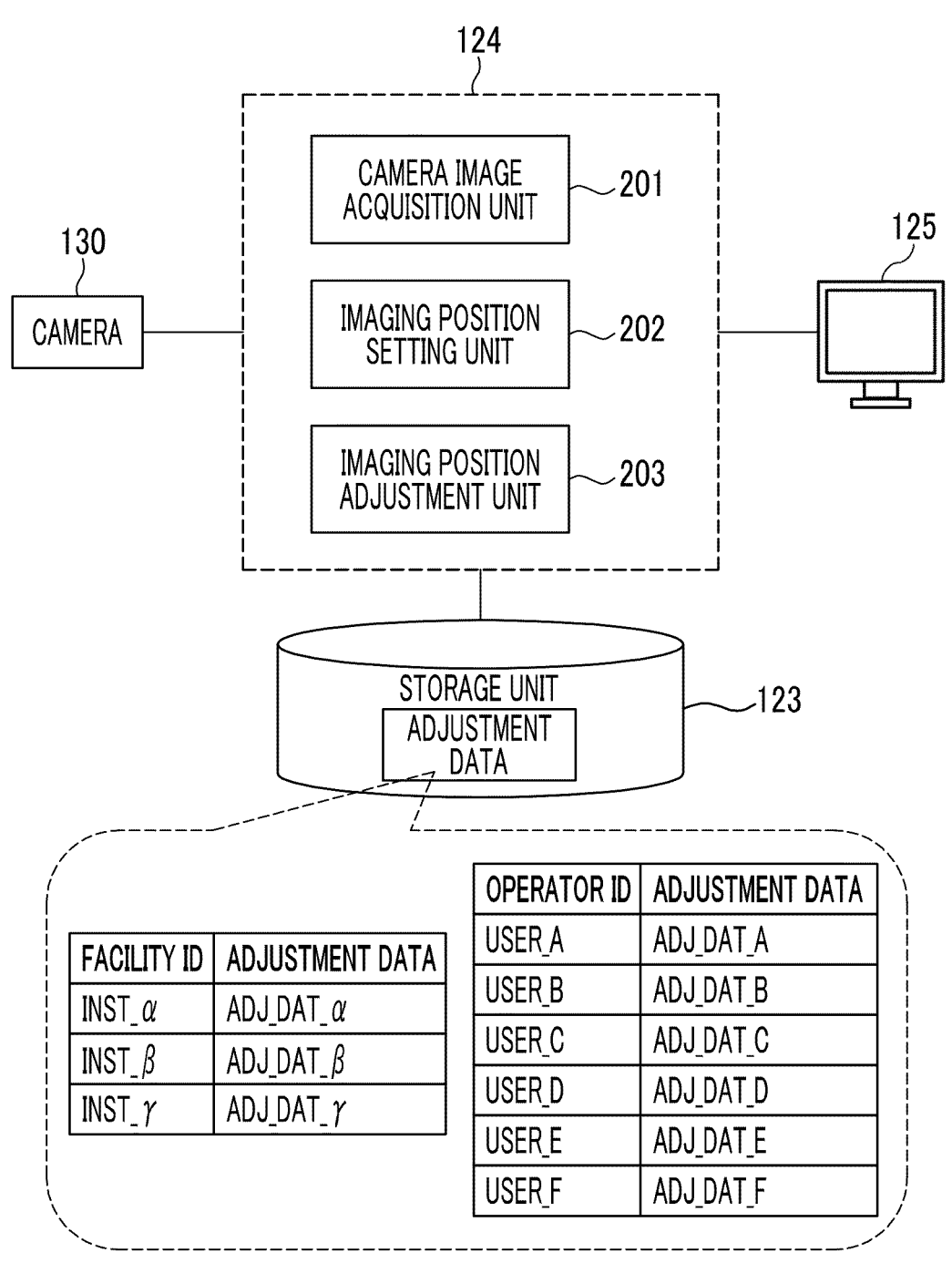
FIG. 2 is a diagram showing an example of functional blocks of Example 1.

The functional blocks of Example 1 will be described with reference to FIG. 2. It should be noted that these functional blocks may be configured with dedicated hardware using an application specific integrated circuit (ASIC), a field-programmable gate array (FPGA), or the like, or may be configured with software that operates on the system controller 124. In the following description, a case where the functional blocks of Example 1 are configured with software will be described.

In Example 1, a camera image acquisition unit 201, an imaging position setting unit 202, and an imaging position adjustment unit 203 are provided. Hereinafter, each unit will be described. The storage unit 123 stores the adjustment data to be used to adjust the imaging position. The adjustment data is stored for each facility ID or for each operator ID, which is an identifier for identifying the facility or operator. FIG. 2 illustrates a table in which the facility ID or the operator ID is associated with the adjustment data.

The camera image acquisition unit 201 acquires the camera image captured by the camera 130. The acquired camera image is a digitized image and is a still image or a frame image in a video.

The imaging position setting unit 202 sets the imaging position with respect to the subject 10 based on the camera image acquired by the camera image acquisition unit 201. For example, the imaging position setting unit 202 sets the imaging position based on an examination site and a shape of the subject 10 extracted from the camera image. More specifically, in a case where the examination site is a chest part, the imaging position is set based on the positions of the jaw and the shoulders estimated from the shape of the subject 10 on the camera image. Further, the imaging position setting unit 202 may be a machine learning engine that has been trained through machine learning using a shape of a human body and an imaging position for each examination site.

The imaging position adjustment unit 203 adjusts the imaging position set by the imaging position setting unit 202 by using the adjustment data stored in the storage unit 123. The adjustment data is read out according to the facility ID or the operator ID.

Figure 3:
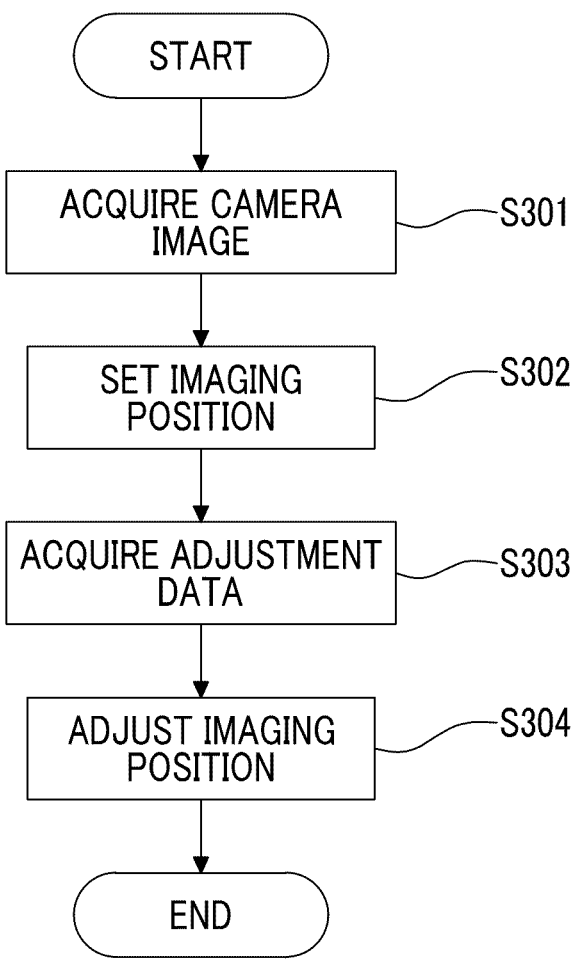
FIG. 3 is a diagram showing an example of a flow of processing of Example 1.

An example of a flow of processing of Example 1 will be described step by step with reference to FIG. 3.

S301

The camera image acquisition unit 201 acquires the camera image in which the subject 10 placed on the examination table 105 is imaged. The camera image acquired in S301 is a still image or a frame image, and may be a camera image transmitted from the camera 130 or a camera image read out from the storage unit 123.

S302

The imaging position setting unit 202 sets the imaging position with respect to the subject 10 by using the camera image acquired in S301. The imaging position is set, for example, based on the examination site and the shape of the subject 10 extracted from the camera image.

Figure 4:
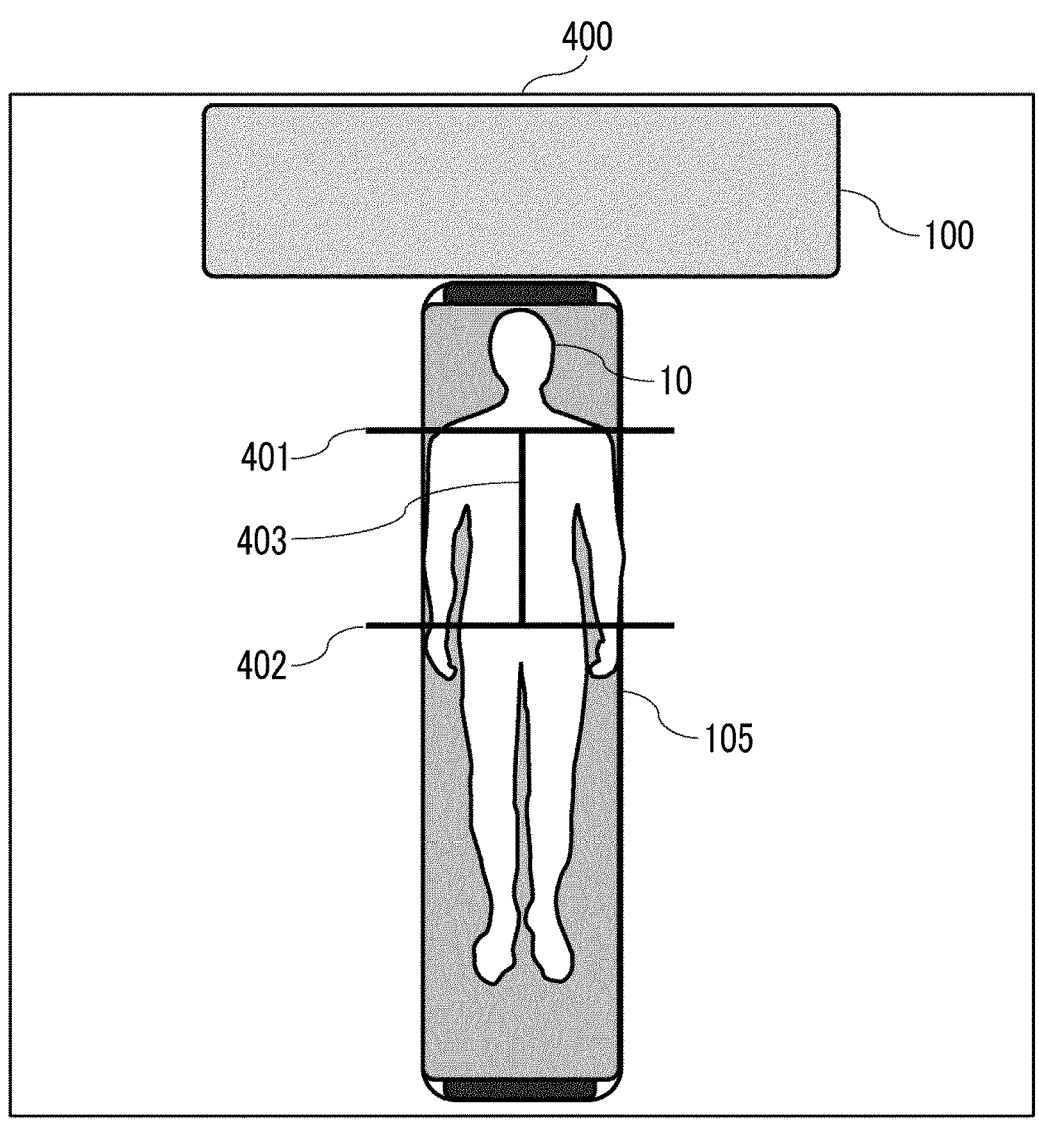
FIG. 4 is a diagram showing an example of an imaging position set based on a camera image.

FIG. 4 shows an example of the imaging position set for a camera image 400 acquired in S301. The camera image 400 illustrated in FIG. 4 includes the scan gantry unit 100, the subject 10, and the examination table 105, and the imaging positions, such as an imaging start position 401, an imaging end position 402, and an imaging center position 403, are set with respect to the subject 10.

S303

The imaging position adjustment unit 203 acquires the adjustment data stored in advance in the storage unit 123 based on the facility ID or the operator ID. The facility ID or the operator ID is input through the input unit 121 in a case where the operator starts the operation of the X-ray CT apparatus.

S304

The imaging position adjustment unit 203 adjusts the imaging position set in S302 by using the adjustment data acquired in S303. For example, the imaging position is adjusted by adding the adjustment data to the imaging position set in S302. An adjusted imaging position is displayed on the display unit 125.

Figure 5:
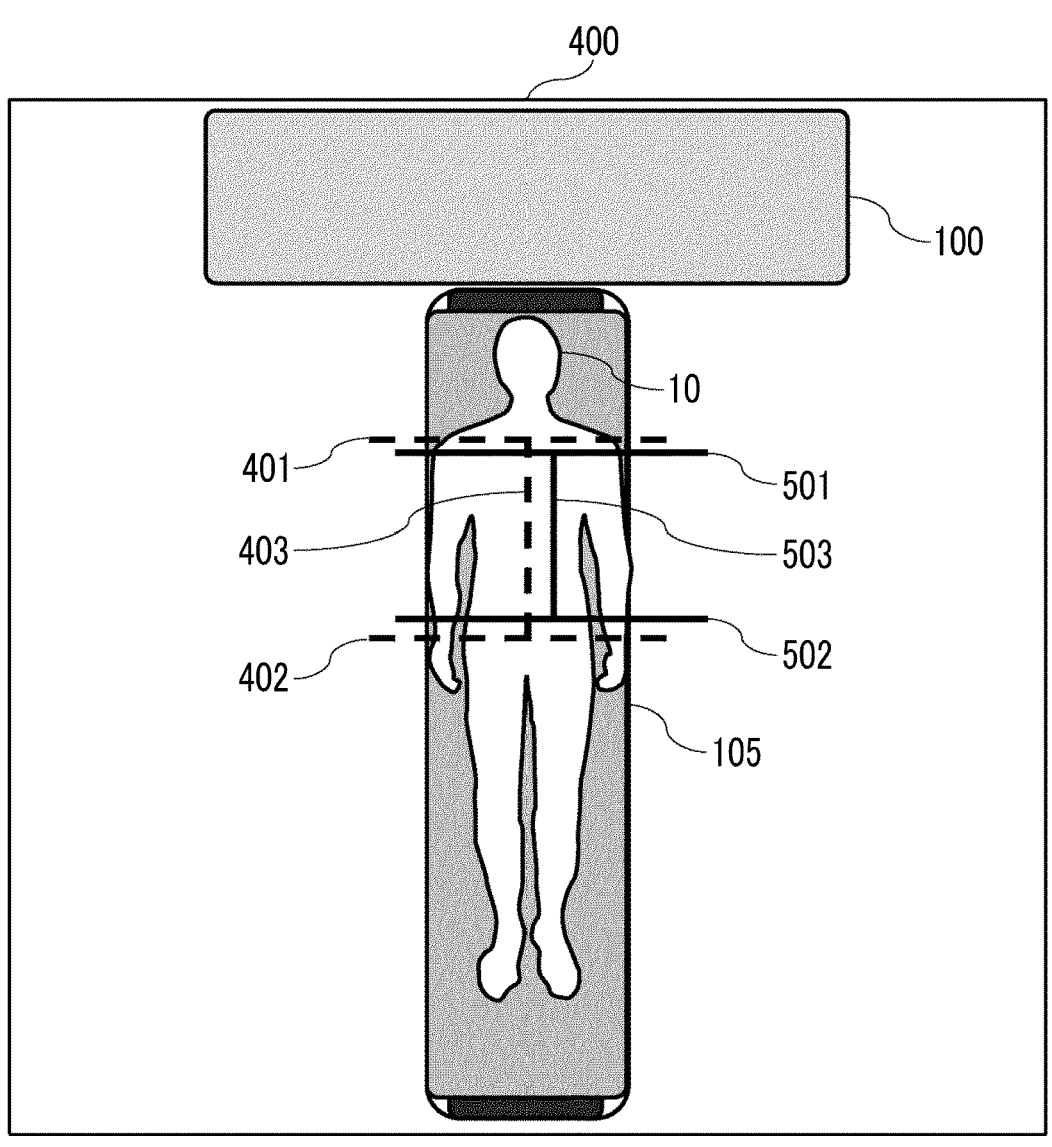
FIG. 5 is a diagram showing a display example of an adjusted imaging position.

FIG. 5 shows a display example of the adjusted imaging position. FIG. 5 shows adjusted imaging positions, such as an adjusted imaging start position 501, an adjusted imaging end position 502, and an adjusted imaging center position 503, on the camera image 400 illustrated in FIG. 4. In FIG. 5, the imaging start position 401, the imaging end position 402, and the imaging center position 403 are indicated by dashed lines as comparison targets with the adjusted imaging positions. The imaging start position 401, the imaging end position 402, and the imaging center position 403 need not be displayed on the display unit 125. The adjusted imaging position is not limited to the display using the line as shown in FIG. 5 and may be displayed using numerical values indicating the coordinates of the adjusted imaging position on the examination table 105.

Through the flow of the processing described with reference to FIG. 3, the imaging position set by the imaging position setting unit 202 based on a uniform standard is adjusted for each facility or each operator, so that the need for the adjustment of the imaging position by the operator is eliminated. As a result, the burden on the operator can be reduced and the examination workflow can be improved. The operator may readjust the adjusted imaging position, and the readjusted imaging position is reflected in the adjustment data.

Figure 6:
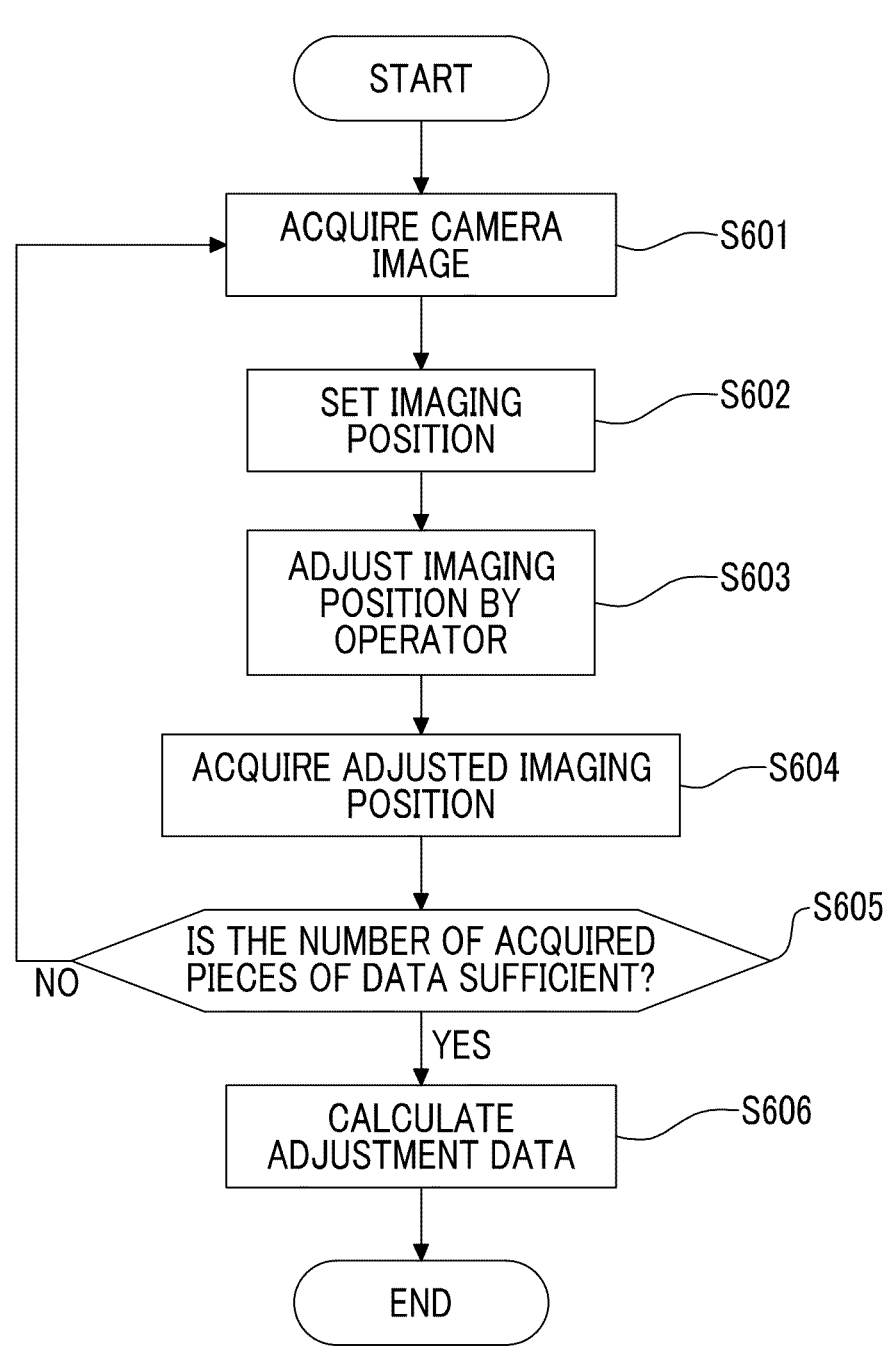
FIG. 6 is a diagram showing an example of a flow of processing of calculating adjustment data.

An example of a flow of processing of calculating the adjustment data will be described step by step with reference to FIG. 6. The readjusted imaging position is also reflected in the adjustment data through the flow of the processing illustrated in FIG. 6.

S601

The camera image acquisition unit 201 acquires the camera image in which the subject 10 placed on the examination table 105 is imaged, in the same manner as in S301.

S602

The imaging position setting unit 202 sets the imaging position with respect to the subject 10 by using the camera image acquired in S601, in the same manner as in S302. The imaging position set in S602 may be the imaging position adjusted by the imaging position adjustment unit 203.

S603

The operator confirms the imaging position set in S602 and adjusts the imaging position as necessary. In a case where the imaging position set in S602 is the imaging position adjusted by the imaging position adjustment unit 203, the imaging position is readjusted. An operation screen displayed on the display unit 125 may be used for the adjustment or readjustment of the imaging position.

Figure 7:
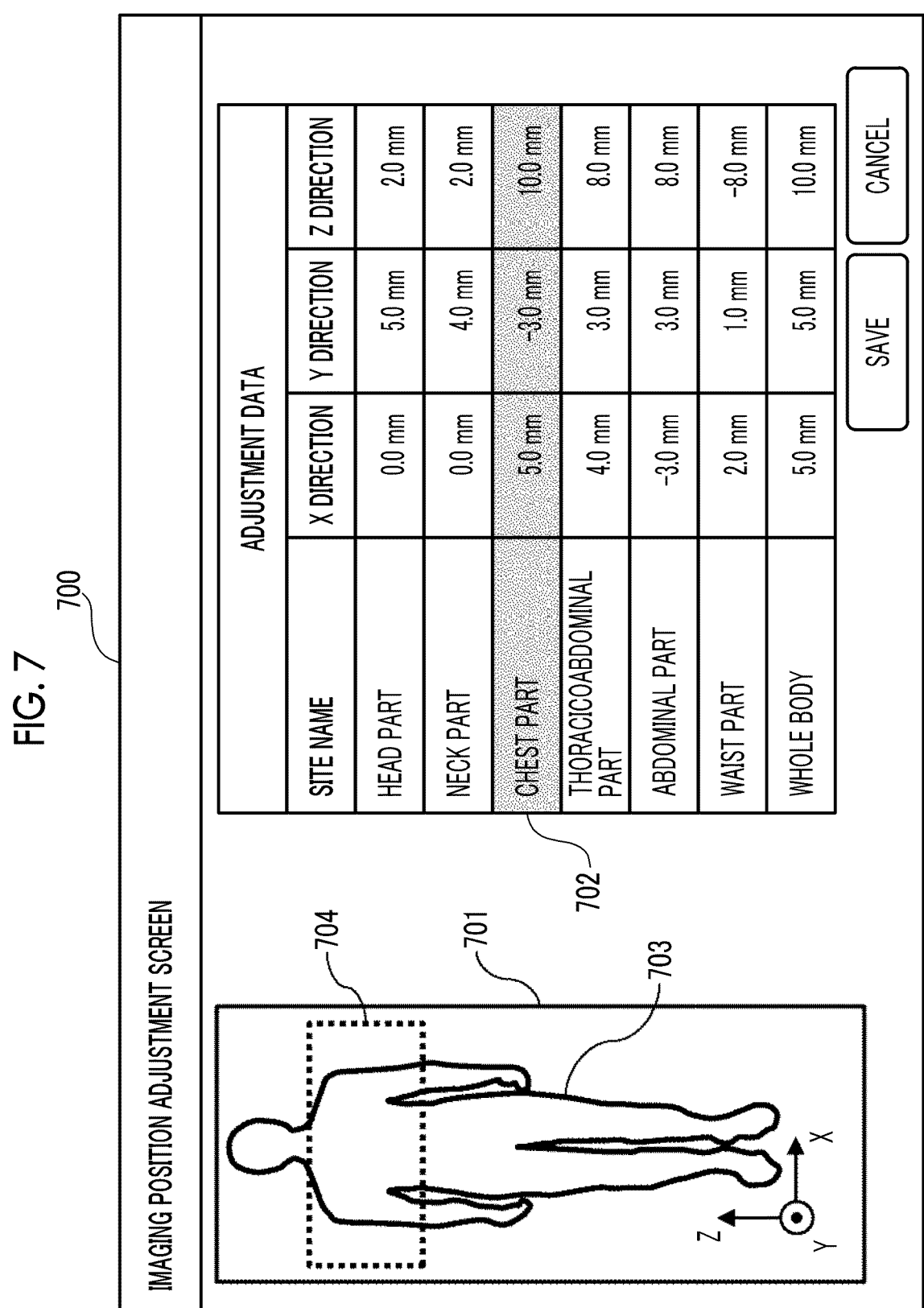
FIG. 7 is a diagram showing an imaging position adjustment screen which is an example of an operation screen.

An imaging position adjustment screen 700, which is an example of the operation screen, will be described with reference to FIG. 7. The imaging position adjustment screen 700 has a human body diagram 701 and an adjustment data table 702 and is operated via the input unit 121.

In the human body diagram 701, a human body outer shape 703 and an imaging range 704 are displayed. The human body outer shape 703 is a figure simulating the outer shape of the human body. The imaging range 704 is an example of a figure showing the imaging position, is indicated by a dashed rectangle in FIG. 7, and is overlaid on the human body outer shape 703. The operator adjusts the size of the imaging range 704 or the relative position of the imaging range 704 with respect to the human body outer shape 703 via the input unit 121. By using the human body diagram 701, the operator can intuitively adjust the imaging range 704. In the human body diagram 701, the imaging position set by the imaging position setting unit 202 may be displayed as a comparison target of the imaging range 704.

In the adjustment data table 702, the adjustment data for the imaging position set by the imaging position setting unit 202 is shown as a numerical value in each of an X direction, a Y direction, and a Z direction, which are three directions orthogonal to each other, for each site. In the adjustment data table 702 of FIG. 7, a row of the chest part is selected, which indicates that the adjustment data of the chest part is being adjusted. The imaging range 704 of the human body diagram 701 and the numerical value of the adjustment data table 702 may be linked to each other so that adjustment made in one may lead to adjustment in the other.

The adjustment of the imaging position is not limited to the adjustment using the operation screen. For example, the imaging position may be adjusted through a gesture by an operator in the vicinity of the subject 10. Since the operator in the vicinity of the subject 10 cannot operate the input unit 121 of the operation unit 120, the adjustment of the imaging position through the gesture is effective.

The gesture by the operator is imaged by the camera 130, and the type of the gesture is classified through analysis of the captured camera image. For example, a gesture, such as pointing the thumb upward with the palm closed and moving the hand to the imaging position that the operator wants to adjust, may be used, or a gesture, such as pointing the index finger at the imaging position that the operator wants to adjust, may be used. In addition, the adjustment of the imaging position through the gesture may be started in a case where a predetermined phrase is spoken or in a case where the operator waves the hand to the camera 130. Further, a combination with other gestures or a combination with the operation on the operation screen or a hardware button may be made.

S604

The imaging position adjustment unit 203 acquires the imaging position adjusted in S603. The imaging position acquired in S604 is stored in the storage unit 123 in association with the facility ID, the operator ID, the site, or the like.

S605

The imaging position adjustment unit 203 determines whether or not the number of acquired pieces of data acquired in S604 is sufficient. The processing proceeds to S605 in a case where the number of acquired pieces of data is sufficient, and the processing returns to S601 in a case where it is insufficient. Whether or not the number of acquired pieces of data is sufficient is determined based on a predetermined threshold value. That is, in a case where the number of acquired pieces of data exceeds the threshold value, it is determined that the number of acquired pieces of data is sufficient.

S606

The imaging position adjustment unit 203 calculates the adjustment data by using the adjusted imaging position acquired in S604. The calculated adjustment data is stored in the storage unit 123 in association with the facility ID, the operator ID, the site, or the like.

The adjustment data is, for example, an average value, a median value, or a mode value of a plurality of pieces of data acquired in S604. It is preferable that the average value, the median value, or the mode value is calculated for each facility ID, each operator ID, or each site. In a case where the average value, the median value, or the mode value is used as the adjustment data, the time required for calculating the adjustment data can be shortened.

In addition, the output of the machine learning engine, which has been trained through machine learning using the adjusted imaging position as training data, with the facility ID, the operator ID, the site, or the like as an input parameter, may be used as the adjustment data. In a case where the output of the machine learning engine is used as the adjustment data, the adjustment data can be calculated more accurately.

Through the flow of the processing described with reference to FIG. 6, the adjustment data of the imaging position is calculated based on the adjustment by the operator. The calculated adjustment data is used in the flow of the processing illustrated in FIG. 3. By using the adjustment data calculated based on the adjustment by the operator, the imaging position can be adjusted for each facility or each operator.

The plurality of embodiments of the present invention have been described above. The present invention is not limited to the above-described embodiments, and the components can be modified and embodied without departing from the gist of the invention. Additionally, a plurality of components disclosed in the above-described embodiments may be combined as appropriate. Furthermore, some components may be deleted from all the components described in the above-described embodiments.

EXPLANATION OF REFERENCES

10: subject
100: scan gantry unit
101: X-ray source
102: rotating plate
103: collimator
104: opening portion
105: examination table
106: X-ray detector
107: data collection unit
108: rotating plate controller
109: examination table controller
110: X-ray controller
111: high-voltage generation unit
120: operation unit
121: input unit
122: image generation unit
123: storage unit
124: system controller
125: display unit
130: camera
201: camera image acquisition unit
202: imaging position setting unit
203: imaging position adjustment unit
400: camera image
401: imaging start position
402: imaging end position
403: imaging center position
501: adjusted imaging start position
502: adjusted imaging end position
503: adjusted imaging center position
700: imaging position adjustment screen
701: human body diagram
702: adjustment data table
703: human body outer shape
704: imaging range

What is claimed is:

1. A medical image capturing apparatus that captures a medical image of a subject, the medical image capturing apparatus comprising:

a camera image acquisition unit that acquires a camera image in which the subject placed on an examination table is imaged;

an imaging position setting unit that sets an imaging position based on the camera image;

a storage unit that stores adjustment data related to the imaging position for each facility or for each operator, wherein the adjustment data comprises values included in an adjustment data table, the values indicating coordinates of the imaging position on the examination table, and the values in the adjustment data table are linked to the imaging position; and a processor is configured to adjust the imaging position by using the adjustment data acquired from the storage unit based on an identifier for identifying the facility or the operator, wherein when the adjusted imaging position is readjusted, the readjusted imaging position is reflected in the values of the adjustment data table.

2. The medical image capturing apparatus according to claim 1, wherein the adjustment data is calculated based on adjustment by the operator for the imaging position set by the imaging position setting unit or for the imaging position adjusted by the processor.

3. The medical image capturing apparatus according to claim 2, wherein the adjustment by the operator is made by adjusting, on an operation screen having a human body outer shape and an imaging range displayed by being overlaid on the human body outer shape, a size of the imaging range or a relative position of the imaging range with respect to the human body outer shape.

4. The medical image capturing apparatus according to claim 2, wherein the adjustment by the operator is made through a gesture by an operator in a vicinity of the subject.

5. The medical image capturing apparatus according to claim 2, wherein the adjustment data is an average value, a median value, or a mode value of a plurality of pieces of data acquired through the adjustment by the operator.

6. The medical image capturing apparatus according to claim 2, wherein the adjustment data is an output of a machine learning engine that has been trained through machine learning using data acquired through the adjustment by the operator as training data, with the identifier or a site as an input parameter.

7. A control method of a medical image capturing apparatus that captures a medical image of a subject, the control method comprising:

a camera image acquisition step of acquiring a camera image in which the subject placed on an examination table is imaged;

an imaging position setting step of setting an imaging position based on the camera image; and an imaging position adjustment step of adjusting the imaging position by using adjustment data related to the imaging position, the adjustment data being acquired based on an identifier for identifying a facility or an operator from a storage unit that stores the adjustment data for each facility or for each operator, wherein the adjustment data comprises values included in an adjustment data table, the values indicating coordinates of the imaging position on the examination table, and the values in the adjustment data table are linked to the imaging position, and when the adjusted imaging position is readjusted, the readjusted imaging position is reflected in the values of the adjustment data table.

\* \* \* \* \*